(12) United States Patent
Sinelnikov

(10) Patent No.: US 10,039,566 B2
(45) Date of Patent: Aug. 7, 2018

(54) ULTRASONIC TRANSDUCER ASSEMBLY

(71) Applicant: MISONIX, INCORPORATED, Farmingdale, NY (US)

(72) Inventor: Yegor Sinelnikov, Port Jefferson, NY (US)

(73) Assignee: MISONIX, INCORPORATED, Farmingdale, NY (US)

( * ) Notice: Subject to any disclaimer, the term of this patent is extended or adjusted under 35 U.S.C. 154(b) by 15 days.

(21) Appl. No.: 14/192,297

(22) Filed: Feb. 27, 2014

(65) Prior Publication Data

US 2014/0180102 A1 Jun. 26, 2014

Related U.S. Application Data

(62) Division of application No. 13/203,771, filed as application No. PCT/US2011/000911 on May 20, 2011, now Pat. No. 8,690,783.

(60) Provisional application No. 61/403,997, filed on Sep. 24, 2010, provisional application No. 61/396,116, filed on May 21, 2010.

(51) Int. Cl.

| *A61B 8/00* | (2006.01) |
| *A61B 17/32* | (2006.01) |
| *A61B 8/12* | (2006.01) |
| *G01N 29/22* | (2006.01) |
| *G01N 29/24* | (2006.01) |

(52) U.S. Cl.

CPC ........ *A61B 17/320068* (2013.01); *A61B 8/12* (2013.01); *A61B 8/4209* (2013.01); *A61B 8/445* (2013.01); *A61B 8/4488* (2013.01); *A61B 8/4494* (2013.01); *G01N 29/221* (2013.01); *G01N 29/2437* (2013.01)

(58) Field of Classification Search
CPC .................................. A61B 8/12; A61N 7/02
See application file for complete search history.

(56) References Cited

U.S. PATENT DOCUMENTS

| 8,414,494 B2 | 4/2013 | Vaezy et al. |
| 2001/0003788 A1 | 6/2001 | Ball et al. |
| 2001/0031922 A1* | 10/2001 | Weng .................. A61B 17/0057 600/439 |
| 2002/0135273 A1 | 9/2002 | Mauchamp et al. |
| 2004/0082859 A1* | 4/2004 | Schaer ................. A61B 8/4281 600/459 |

(Continued)

FOREIGN PATENT DOCUMENTS

JP 2003-339706 12/2003

*Primary Examiner* — Hien Nguyen
(74) *Attorney, Agent, or Firm* — R. Neil Sudol; Henry D. Coleman

(57) ABSTRACT

An ultrasound transducer assembly includes an acoustic focusing lens and a therapy transducer mounted to a holder member so that the lens is movable relative to the transducer. The lens and the transducer are mounted to the holder member so that the lens is spaced a predetermined distance from the transducer element. A liquid layer having a thickness of the predetermined distance is provided between the lens and the transducer element. A solid backing member is disposed on a side of the transducer element opposite the lens. The backing member is spaced by an additional liquid layer of a predetermined thickness from the transducer element. The focusing depth of the lens-transducer assembly is controllable by transducer operating frequency.

13 Claims, 11 Drawing Sheets

(56) References Cited

U.S. PATENT DOCUMENTS

| | | | |
|---|---|---|---|
| 2004/0215079 A1 | 10/2004 | Omura et al. | |
| 2004/0254570 A1* | 12/2004 | Hadjicostis et al. | 606/27 |
| 2005/0184624 A1 | 8/2005 | Hasegawa et al. | |
| 2006/0058707 A1* | 3/2006 | Barthe | A61B 8/4272 601/2 |
| 2007/0016063 A1* | 1/2007 | Park | A61M 25/0158 600/459 |
| 2007/0232922 A1* | 10/2007 | Kohno | A61B 1/018 600/459 |
| 2009/0036774 A1* | 2/2009 | Weng | A61B 8/12 600/439 |
| 2009/0299360 A1* | 12/2009 | Ormsby | A61B 8/0841 606/33 |

* cited by examiner

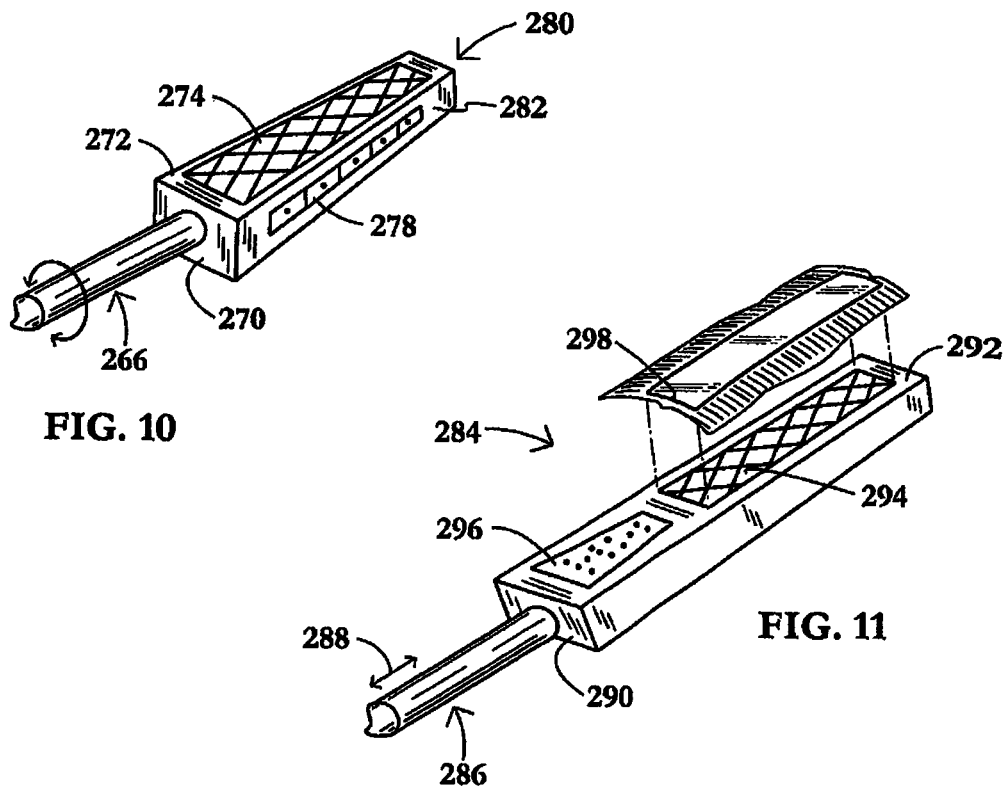
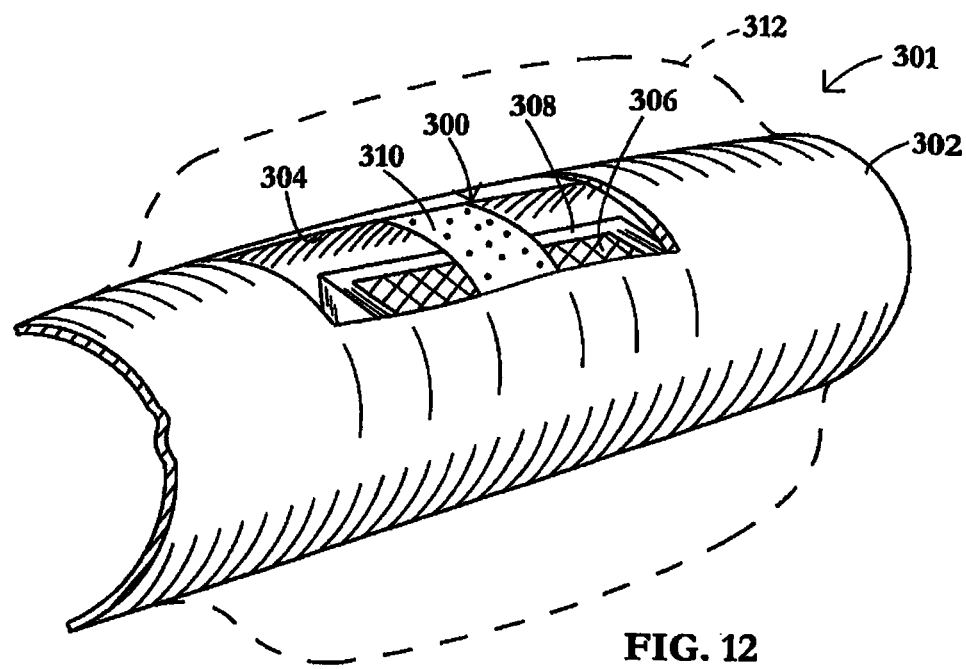

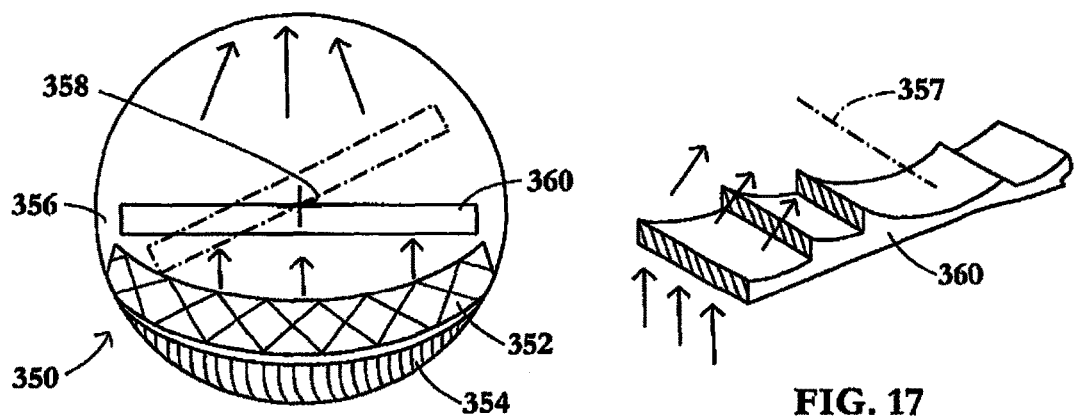
FIG. 16
FIG. 17
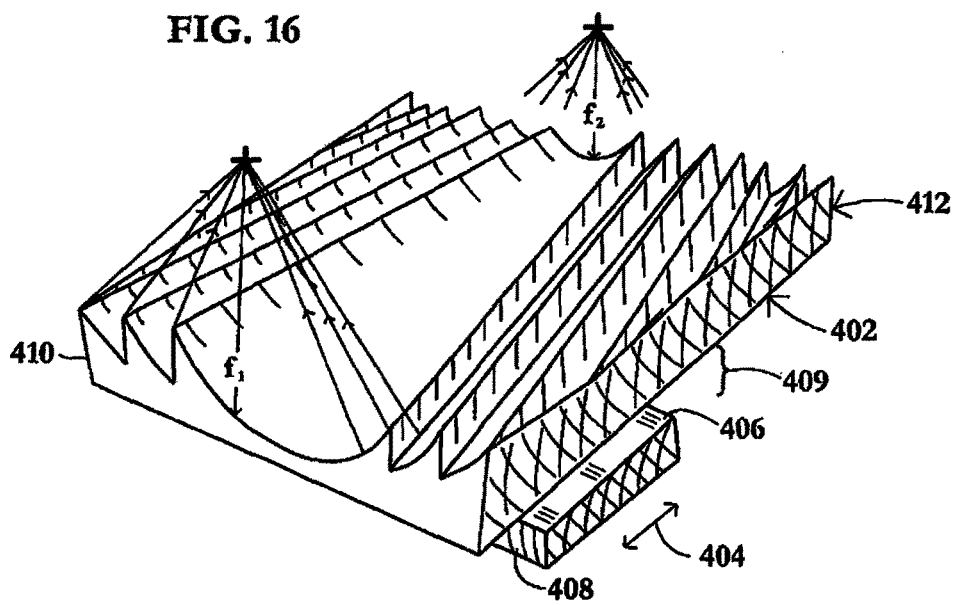
FIG. 18
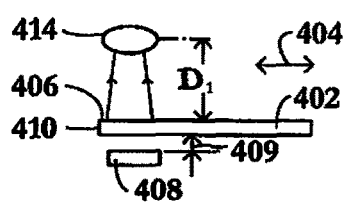
FIG. 19A
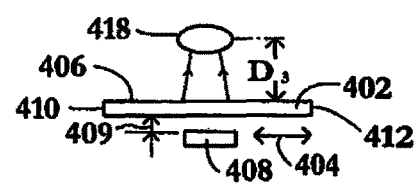
FIG. 19B

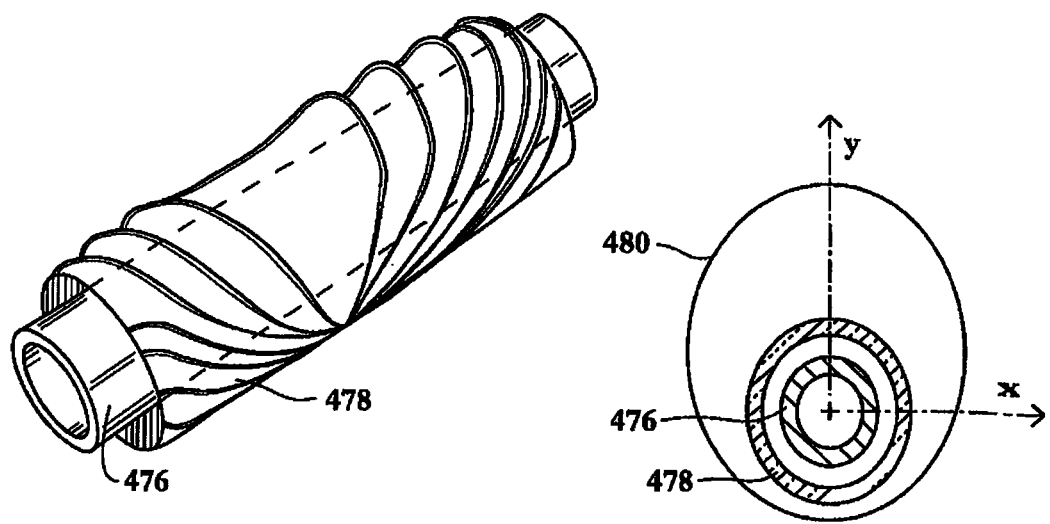
FIG. 29
FIG. 30
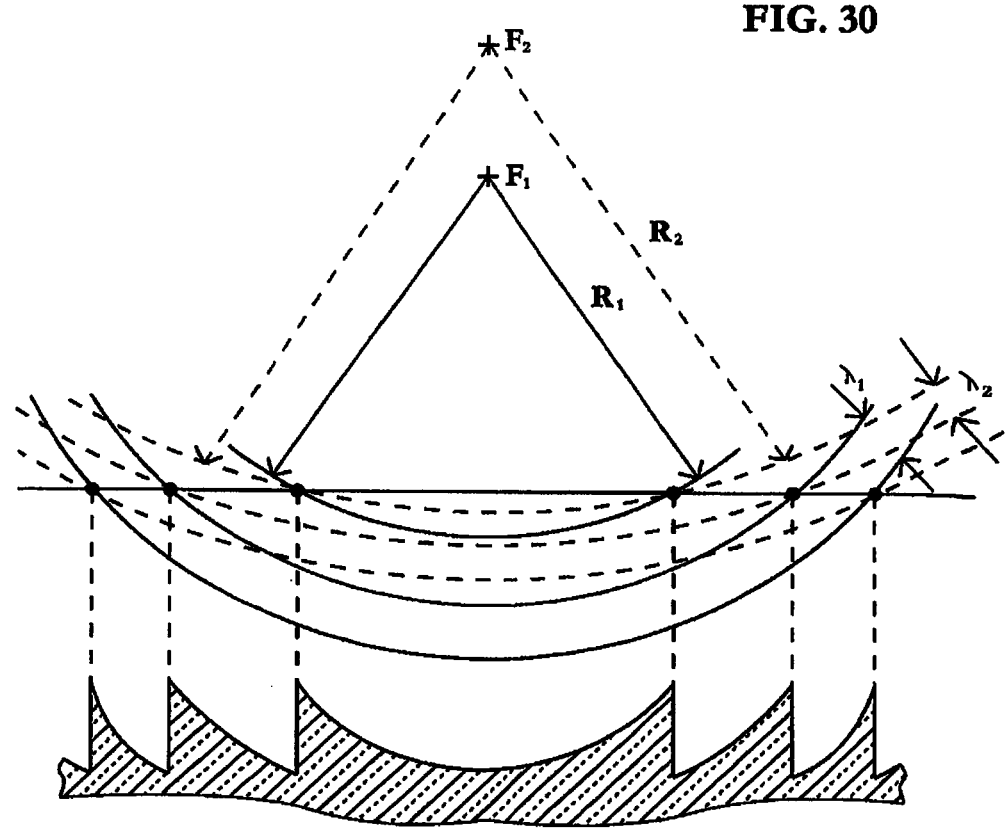
FIG. 31

ULTRASONIC TRANSDUCER ASSEMBLY

CROSS-REFERENCE TO RELATED APPLICATION

This application is a division of application Ser. No. 13/203,771 filed Aug. 29, 2011, now U.S. Pat. No. 8,690,783.

FIELD OF THE INVENTION

This invention relates to an ultrasonic transducer assembly. The invention is particularly useful in medical diagnostic and therapeutic applications.

BACKGROUND OF THE INVENTION

Ultrasound is widely used in modern medicine for diagnostics and minimally invasive treatment in such fields as obstetrics, cardiology, endocrinology, gastroenterology, neurology, ophthalmology, urology, osteoporosis, and clinical diagnostics. Ultrasound diagnostics uses low-power ultrasonic scanners for investigation and visualization of inner organs, tissue layers and structures, for determination of blood flow direction and velocity, for measurement of density and other parameters of tissues, and for detection of cancer and other tumors. In diagnostics, acoustic lenses have been traditionally used in pulse mode to manipulate the wave front propagation delays. In therapeutic applications, continuous ultrasound waves with an average acoustic intensity of up to several watts per centimeter square at the transducer surface are typically used to focus ultrasound. The focused ultrasonic waves produce highly localized and intense acoustic fields, up to several hundreds of watts in power density, and enable controlled, deep-reaching and localized treatment of malignant tissues, with few secondary effects for surrounding health tissues. It is beneficial to control ultrasonic energy deposition for quickly overheating target focal tissue while minimizing the impact on surrounding non-targeted tissues. The mastery of focusing determines the success of therapy and requires an understanding of the vibration condition of the radiating surface and thermal and mechanical constraints. Because acoustic focusing is an interference phenomenon, the phase of individual ultrasound rays becomes a controlling factor in a continuous therapy mode. In a diagnostic imaging mode, focusing limits the beam width and constrains the acoustic energy content of the beam to a smaller cross sectional area, hence improving imaging sensitivity. In this mode, the beam is typically focused using a fixed lens that just bends acoustic rays and preserves the pressure-time waveform of incoming signals. Imaging lenses are used in pulsed mode where their function relies primarily on determining and manipulating the wave front propagation delays. For therapeutics, the mode of operation is typically continuous wave, in which case the phase becomes an important lens design factor as opposed to wave front propagation delay. Traditional convex or concave lenses (Folds, Focusing properties of solid ultrasound cylindrical lenses, 53, 3, pp 826-834, 1973) that converge light rays towards the lens principal axis offer a simple method to focus low power acoustic energy in both therapy and imaging. However, high acoustic absorption in thicker regions of the lenses and excessive heat build up result in a poor lens longevity and large focusing aberration when attempts are made to focus high power acoustic energy in a continuous regime. Hence, thin focusing lenses with discrete phase shifts are both permissible and beneficiary in therapy, greatly reducing overall lens depth profile and allowing different designs, including zone plate Fresnel (Hadimioglu et al, 1993), multilevel (Chan et al, Finite element analysis of multilevel acoustic Fresnel lenses, Vol 43, 4, 1996), field conjugate (Lalonde and Hunt, Variable frequency field conjugate lenses for ultrasound hyperthermia, 42, 5, 825-831, 1995) and other designs (Rosenberg, High intensity ultrasound, Moscow, pp 69-91, 1949; Tarnoczy, Sound focusing lenses and waveguides, Ultrasonics, 115-127, 1965).

Discrete phase acoustic focusing lenses in combination with flat transducers or arrays offer an elegant and cost effective solution for hyperthermia treatment of cancer and tumors, where the tissue is heated using ultrasound to temperatures of 43-45° C. for several minutes. It is well known that tumor cells become much more susceptible to radiotherapy and chemotherapy under elevated temperature. In physiotherapy lens focused ultrasound may be used to increase the elasticity of sinews and scars, improve the mobility of joints, provide analgesic effects, alter blood flow, and produce muscular spasms. High intensity ultrasound (10-2000 W/cm$^2$) is used for tissue ablation, cutting, fractionation (histotripsy) and for arresting internal bleeding (hemostasis). Historically, piezoelectric and magnetostrictive transducers are widely used to transform generate a high intensity ultrasound field.

In therapeutic applications the precision targeting of deep tissues is important. Desired therapeutic effect must be confined to a small spot within the body where temperature elevation is sufficient to create a localized tissue impact without affecting surrounding tissue and organs. This technique is used to selectively destroy the unwanted tissue within the body without perturbing adjacent tissues. Typically, heating the tissue to 60° C.-80° C. results in tissue necrosis, a process commonly termed as thermal ablation. In most cases, the high intensity focused ultrasound is used in thermal ablation procedures. Ultrasound focusing can be achieved by having concave focused transducers producing convergent beams of predetermined geometry and/or by manipulating the driving electrical signals (phase and amplitude) of multiple active transducers (Cathignol, 2002, High Intensity Piezoelectric Sources for Medical Applications: Technical Aspects, *Nonlinear Acoustics at the Beginning of the 21$^{st}$ Century*, 1, 371-378.). Single focused elements are more economical but require mechanical steering and suffer a loss of acoustic efficiency due to heating and presence of parasitic surface waves (Kluiwstra et al., 1997, Design Strategies for Therapeutic Ultrasound Phased Arrays, SPIE International Medical Imaging Symposium, Chapelon et al. Transducers for therapeutic ultrasound, *Ultrasound in Med. & Biol.*, Vol. 26, No. 1, pp. 153-159, 2000).

Ultrasound systems use relatively small, low-power transducers for diagnostic visualization and large high-power transducers for therapy. Typically, the radiation surfaces of the two types of transducers coincide and often form a surface of revolution of a conic section: circle, ellipse or parabola. Transducers with large radiating surfaces are used to generate sufficient acoustic power and are expensive to manufacture. Additionally, the applicability of large concave transducers is limited to an open field clinical cases, where the size of the transducer does not matter, as opposed to the most intra-luminal or intra-cavity applications, where access is limited and the dimensional requirements counter acoustic power and sensitivity requirements.

SUMMARY OF THE INVENTION

The present invention aims to provide an improved focused ultrasound transducer assembly. The transducer of the present invention provides an alternative for ultrasound focusing at different depths in a subject for ultrasound scanning and therapy.

The present invention in part aims to provide an ultrasound transducer with a substantially flat radiating shape and an interchangeable disposable focusing lens to provide an alternative for ultrasound focusing at different depths in tissue for ultrasound visualization and therapy.

This invention is directed in principal part to an apparatus and method for applying sonic energy within the body of the living subject. More particularly, this invention is directed in principal part to a probe for applying ultrasound energy within the body of a subject and that includes a probe body having a proximal end and a distal end that is adapted for insertion into the body of a subject. The probe further includes an ultrasound transducer disposed proximate to the distal end of the probe body and a device for moving one portion of the transducer relative to the probe body while the distal end of the probe is disposed within the body of the subject. The ultrasound transducer typically includes a set of piezoelectric elements having an essentially flat front radiating surface. The probe further includes an interchangeable lens for focusing an ultrasound wave. The lens is disposed in the front of the piezoelectric elements parallel to their radiating surface and is movable relative to the piezoelectric elements to focus ultrasound energy at different locations. A set of piezoelectric elements has an arrangement of electrodes enabling its use for diagnostic investigations and therapeutic applications.

One aspect of the present invention provides a substantially flat set of ultrasonic transducers conveniently sized for passage into and/or through body cavities and lumens and optimized for acoustic power efficiency to effectively visualize and/or treat internal organs or regions of the body. One form of such transducer includes one or a plurality of discrete transducers elements mounted in a layered structure with a substrate or backing layer and with cooling produced by channeling water through one or more gaps between the layers of the transducer assembly, the gaps being of predefined size to maximize the forward acoustic power. A further aspect of present invention provides a disposable lens attachable to such a transducer in order to focus ultrasound at a single spot or multiple spots for therapeutic and diagnostic applications. Such a disposable lens can be manufactured at a low cost in a variety of focusing configurations. It shall provide doctors with an additional set of reliable tools to deliver configurable ultrasound energy focusing based on a patient's anatomy. One form of the lens variation can be interchangeable Fresnel lenses of substantially similar dimensions designed to focus at different tissue depths. The depth of focus can be controlled by a mechanical exchange of different focal length lenses or by adjusting the transducer operating frequency. In the latter case, the Fresnel lens changes its depth of focus depending on the frequency thus offering an elegant way of controlling energy deposition at different depths when treating large tissue volumes using a single fixed lens and a set of high-power transducers capable of operating at a range, or with a discrete set, of frequencies. This option is particularly attractive because it does not require any device constituent components exchanges and can be fully controlled electronically. FIG. 24 shows relative intensity profiles created by the 8-zones Fresnel at a set of frequencies. The lens was designed to focus 4 MHz waves at 40 mm depth. Clearly, the use of 5 MHz frequency moves the focal zone deeper, outward by about 10 mm, while focal spot is brought to a shallower depth at 3 MHz. This invention further contemplates moving the transducer relative to a lens or both relative to a probe in order to achieve large volume tissue impact.

As yet another alternative, a field conjugate lens (Lalonde and Hunt, Variable frequency field conjugate lenses for ultrasound hyperthermia, 42, 5, 825-831, 1995) for simultaneous focusing of an acoustic field in multiple locations can provide a volume distributed focal pattern that can enable stationary ablation of large tissue volumes.

The present invention contemplates that one or more imaging transducer elements and one or more therapeutic transducer elements are integral parts of a transducer assembly. The imaging and therapeutic transducer elements are either adjacent to and joined to one another or located in close proximity. The device may further comprise a probe casing, a lens, and a holder. The lens and the transducer module may be mounted to the holder inside the probe casing.

In accordance with a feature of the present invention, a lens and a therapy transducer are mounted to a holder assembly with the lens inserted in front of the transducer to thereby create a desirable focal pattern (spot, multiple spots, line, or spatially distributed pattern) in accordance with a diagnosis of a diseased organ to be treated with therapeutic ultrasound. The lens according to this aspect of invention is made of material such as polystyrene, polyethylene, parylene, nylon, or acrylic or combinations thereof, that has a sound speed higher than that of water, or Flourinert liquid, contained in a thin wall mold or low absorption moldable silicone rubbers, such as in RTV-615 family, offering a lens design with sound speed lower than that of water. The lens may be disposable and has a potential to be geometry compliant to a desired shape and form, if made out of flexible material such as silicone.

Another aspect of this invention includes a lens movable relative to the transducer to thereby vary the location of a focal zone relative to the transducer. The movability of the lens facilitates the application of ultrasonic waveform energy to an extended surgical target region. The lens may be movable in parallel to a planar transducer element, which facilitates the targeting of a planar tissue structure.

The lens may constitute a thin sheet not exceeding several ultrasound wavelengths in thickness and a few times larger than the transducer to expose different sections of the sheet when it is moved over an active area of the transducer. The sheet my contain a continuously varying imprinted lens pattern or a plurality of discretely varying imprinted lens patterns that provide for different focal zones, for example, varying in focal depth, thus enabling simple mechanism to have a device with variable focal length. A Fresnel lens larger than the transducer may enable shifting of the focal pattern from one location to another. Alternatively, separate lens patterns can be imprinted on a sheet to enable focusing at different distances and/or angles and produce spatially distributed multiple focal spot patterns required for an effective and fast ablation procedure.

An ultrasonic transducer device in accordance with the present invention comprises at least one high-intensity ultrasound transducer element made of a piezoelectric ceramic material, an acoustic focusing lens, and a holder assembly. The lens and the module are mounted to the holder assembly so that the lens is spaced a predetermined distance from the transducer element. A liquid layer having a thickness of the predetermined distance is provided between the lens and the transducer element.

The flat transducer sandwiched between two lenses with different focal depth mounted on a holder or fixed parallel to said transducer through a water gap constitute an enabling arrangement to achieve tissue ablation at different depth. The part of the acoustic energy emanated by the transducer toward the tissue, propagate through a lens and is focused at a depth fully defined by the lens design. The other part of the energy is radiated away from the tissue and blocked by the holder or scattered inside a water cooled probe.

Pursuant to another feature of the present invention, this device further comprises a solid backing member disposed on a side of the transducer element opposite the lens. The backing member is spaced by an additional predetermined distance from the transducer element. A liquid layer having a thickness of the additional predetermined distance is provided between the transducer element and the backing member.

Pursuant to a supplemental feature of the present invention, this device may also comprise at least one imaging transducer element made of a piezoelectric polymeric material, the imaging transducer element being bonded to either the high-intensity ultrasound transducer element or the lens. The imaging transducer element may be bonded to a front or rear major surface of the high-intensity ultrasound transducer element or disposed inside a recess therein.

The lens and the transducer element may be mounted to the holder assembly so that the lens is movable relative to the transducer element to thereby enable one to vary the location of a focal locus relative to the holder assembly (and concomitantly relative to the patient, with the probe or holder assembly being held stationary relative to the patient). Where the transducer element has a planar form, the lens may be shiftable in a plane oriented substantially parallel to the transducer element, thereby enabling a relocating of the focal locus in a plane parallel to the transducer element. Where the lens is rotatable about an axis, the focal locus may be repositioned along a cylindrical locus.

Pursuant to an additional feature of the present invention, the device further comprises at least one metal member operatively mounted to the holder assembly laterally of the lens so as to block transmission of ultrasonic vibrations along pathways laterally displaced relative to the lens. Where the lens is movable relative to the transducer, the metal member(s) are stationary with respect to the lens and move therewith relative to the transducer.

An ultrasonic diagnostic and treatment probe in accordance with another feature of the present invention comprises a casing provided at a distal end with a sidewall having a window, a transducer holder disposed inside the probe, at least one high-intensity or high-power therapeutic transducer element made of a piezoelectric ceramic and mounted to the holder so as to be juxtaposable to the window, and at least one imaging transducer element disposed in a region about the window.

It is to be understood that at least the therapeutic transducer element is disposed in a liquid-filled bladder (bolus) which in turn is disposed mainly inside the casing (but potentially extends out through the window in the casing). The liquid-filled bladder enables efficient transmission of ultrasonic pressure waves between target tissues of a patient, on the one hand, and the therapeutic transducer element and possibly the imaging transducer element, on the other hand.

Where the holder is provided with a plurality of faces (for instance, where the holder is in part a right rectangular prism), the holder may be rotatably mounted in the casing so that different ones of the faces may be alternately positioned adjacent to and facing the window. In that case, the high-intensity or high-power therapeutic transducer element may be provided on a first one of the faces, and the imaging transducer element on a second one of the faces. Accordingly, the mode of operation of the probe may be changed from therapy to diagnostic examination and vice versa in part by rotating the holder to juxtapose the appropriate transducer element to the window.

The faces of the probe holder are oriented at a non-zero angle relative to one another. Where the holder includes a right rectangular prism, the therapeutic transducer element and the imaging transducer element may be disposed in faces that are parallel, or alternatively perpendicular, to one another.

Alternatively, where the probe casing and the holder each exhibit a longitudinal axis oriented coaxially or in parallel to one another, the high-intensity or high-power therapeutic transducer element and the imaging transducer element may be disposed along a common side of the holder. In that event, the holder is longitudinally reciprocatable relative to the casing so that high-intensity or high-power therapeutic transducer element and the imaging transducer element are alternatively disposable adjacent the window in the casing.

In another alternative configuration, rather than being provided on a holder inside the casing (and inside the bolus), the imaging transducer element is provided on the casing in juxtaposition to the window. Thus, one or more imaging transducer elements may be disposed on a distal and/or proximal side of the window, or alternatively along a web intermediate of the window (bisecting the window into two openings).

The imaging transducer element is preferably made of a piezoelectric polymeric material such as polyvinylidene fluoride (PVDF). Further materials are discussed hereinafter. As indicated, an acoustic Fresnel lens may be mounted at least indirectly to the casing adjacent to the window for focusing ultrasonic waves from the therapeutic transducer onto a focal locus such as a line or point.

An ultrasonic diagnostic and treatment probe in accordance with yet another feature of the present invention comprises a casing provided at a distal end with a sidewall having a window, at least one high-intensity or high-power therapeutic transducer element made of a piezoelectric ceramic and disposed inside the casing in juxtaposition to the window, and an acoustic focusing lens mounted at least indirectly to the casing adjacent to the window.

The lens may be mounted to the casing so that the lens is movable relative to the transducer element, thereby varying the location of a focal locus relative to the casing. For instance, the lens may be shiftable parallel to a longitudinal axis of the casing, thereby enabling a relocating of the focal locus in a plane parallel to the transducer element. Alternatively or additionally, the lens may be rotatable about an axis parallel to a longitudinal axis of the casing, thereby enabling a relocating of the focal locus along a cylinder.

The transducer element may be planar or cylindrical, and the lens may be cylindrical or spherical.

Pursuant to the above-described embodiments of the present invention, the invention provides in part a multifocal dual mode ultrasonic transducer for use in a medical therapy and imaging apparatus.

The multifocal ultrasonic transducers of the present invention may be used in a diagnostic mode, applying ultrasonic energy within a body of living subject for visualization of body internal organs, and alternately in a therapeutic mode, implementing thermal ablation, hyperthermia, transfection and/or drug delivery. An imaging transducer element as used in the present invention may be made of polymeric piezoelectric materials. Suitable polymeric materials for imaging transducer elements include polyvinylidene fluoride (PVDF), and copolymers of PVDF such as trifluoroethylene (TrFE) with a piezoelectric voltage constant $g_{33} > 100 \times 10^{-3}$ Vm/N. Piezoceramic materials suitable for therapy transducer elements include modifications of BaTiO$_3$, Pb(Ti,Zr)O$_3$ (PZT) and PbNb$_2$O$_6$ ceramics with a high piezoelectric strain constant, $d_{33} > 200 \times 10^{-12}$ m/V.

Pursuant to an additional feature of the present invention, the device further comprises at least one flat transducer assembly element axially symmetrically mounted to the rotatable holder assembly and enclosed between the focusing lenses on both sides so as to focus ultrasound energy on one side and block transmission of ultrasonic vibrations on the other side by means of probe holder that permits energy propagation to the tissue along the predefined pathways. The focal depth of such assembly can be easily change by rotating the transducer—lens assembly 180 degrees inside the holder assembly.

Yet another feature of phase discrete lenses is the ability to change the focal depth with operating frequency. It can be utilized to produce ablation patterns at different depth and enhance treatment of large tissue volumes. For example, the lens designed to operate at 4.0 MHz at 40 mm depth will focus at a deeper depth when operated at frequency exceeding 4.0 MHz. Alternatively a lens can be constructed of the slow materials, such as, for example the Flourinert liquid, and will focus deeper at higher frequencies, thus being especially attractive for the high resolution imaging applications, which can selectively utilize different frequencies for visualization and targeting of organs located at different depths. For small variation of operating frequency f from the lens design frequency $f_0$ the focusing depth of a lens can be expressed as $F = F_0 f_0 / f$, where $F_0$ is the focal depth at the design frequency $f_0$. A combination of Fresnel lens and multiple transducer set, each of which coincides with an area of a single Fresnel zone, provides an ability to perform multiwave imaging and improve an imaging resolution for deep seated organs. The higher frequency signals coming from deeper depth will be focused by a lens to the respective array receiving elements and processed. This is especially attractive for the monitoring of the cavitation and tissue erosion processes accompanied by an emission of broad spectrum and higher frequency harmonics indicative of lesion formation and location in application of high intensity focused ultrasound.

BRIEF DESCRIPTION OF THE DRAWINGS

FIG. 10 is a schematic perspective view of another dual mode transducer assembly with a rotatable holder, in accordance with the present invention.

FIG. 11 is a schematic perspective view of a dual mode transducer assembly with a reciprocatable holder, in accordance with the present invention.

FIG. 12 is a schematic perspective or isometric view of a dual mode transducer assembly with an imaging transducer element disposed on a casing, in accordance with the present invention.

FIG. 16 is a schematic transverse cross-sectional view similar to FIG. 23, showing an alternative transducer assembly.

FIG. 17 is a schematic partial perspective view of a cylindrical Fresnel lens included in the transducer assembly of FIG. 16.

FIG. 18 is a schematic perspective view of an ultrasound transducer assembly in accordance with the present invention, including an ultrasound transducer and a Fresnel lens with a focal length gradient along one major dimension.

FIGS. 19A-19C are a series of diagrams showing variation in a focal length as a function of relative position of the transducer and Fresnel lens of FIG. 18.

FIG. 29 is a schematic perspective view of a cylindrical transducer and associated cylindrical lens in accordance with the present invention.

FIG. 30 is a schematic end view of the transducer and lens of FIG. 29, showing an associated focal locus.

FIG. 31 is a diagram showing wavefronts of two different frequencies directed to respective focal points by a Fresnel lens.

DETAILED DESCRIPTION

Figure 1:
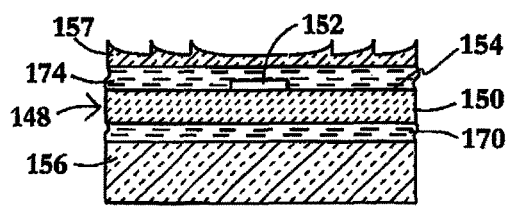
FIG. 1 is a schematic cross-sectional view of a dual mode transducer assembly in accordance with the present invention, showing a backing layer.

As shown in FIG. 1, a dual mode ultrasound transducer assembly or device 148 may comprise a single piezoelectric ceramic transducer element 150 that serves in part as a substrate to one or more piezoelectric polymeric transducer elements 152 bonded to a major face 154 of the ceramic transducer element 150 on a front side thereof, opposite a backing layer 156. Ceramic transducer element 150 functions in a therapy mode of operation to generate high-intensity ultrasonic mechanical vibrations that are transmitted to a desired surgical site inside an organ of a patient. Likewise, polymeric transducer element or elements 152 function in a diagnostic mode of operation to detect incoming ultrasonic pressure waves that are processed to generate image data as to tissue and organ structures of the patient primarily in a region closely about the target surgical site. An acoustic lens 157 may be provided on the front side of transducer 148 (which has a planar front radiating face), opposite backing 156 for focusing at least the therapeutic ultrasonic pressure waves at a focal point (spherical lens) or along a focal line (cylindrical lens). In that case, a single imaging transducer element 150 is provided, which is located in alignment with a center region of lens 157. Lens 157 may be a concave lens, a convex lens, a Fresnel lens, a Fresnel multilevel lens, or a Field Conjugate lens.

Figure 2:
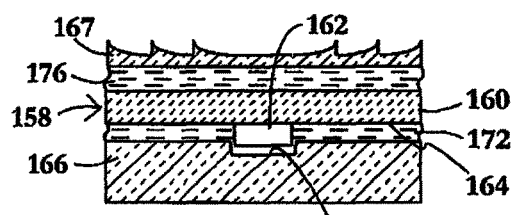
FIG. 2 is a schematic cross-sectional view of yet a further dual mode transducer assembly in accordance with the present invention, showing a backing layer.
Figure 9:
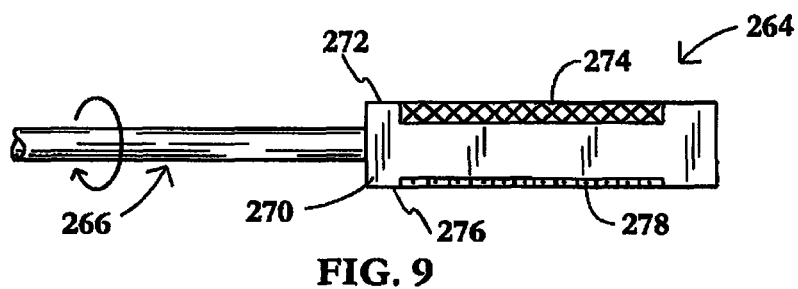
FIG. 9 is a schematic side elevational view of a dual mode transducer assembly with a rotatable holder, in accordance with the present invention.

As shown in FIG. 2, in a modification of ultrasound transducer assembly 148 of FIG. 9, a dual mode ultrasound transducer assembly or device 158 has a single piezoelectric ceramic transducer element 160 serving in part as a substrate to one or more piezoelectric polymeric transducer elements 162 that are bonded to a major face 164 of the ceramic transducer element 150 on a rear side thereof, facing a backing layer 166. The one or more polymeric transducer elements 162 extend into respective recesses 168 formed in backing layer 166. Ceramic transducer element 160 and polymeric transducer element or elements 162 function in alternate operating modes as discussed above. As above, an acoustic lens 167 may be provided on the front side of transducer 158 (which takes a planar form having a planar front radiating face), opposite backing 166 for focusing at least the therapeutic ultrasonic pressure waves at a focal point (spherical lens) or along a focal line (cylindrical lens). In that case, a single imaging transducer element 162 is provided, which is located in alignment with a center region of the lens. Lens 167 may be a concave lens, a convex lens, a Fresnel lens, a Fresnel multilevel lens, or a Field Conjugate lens.

Backing layers 156 and 166 serve in part to reflect ultrasonic pressure waves. Ceramic transducer elements 150 and 160 are spaced from backing layers 156 and 166, respectively, by liquid layers 170 and 172 (typically water or saline) of a thickness selected to facilitate ultrasonic pressure wave transmission, as discussed hereinafter. Likewise, lenses 157 and 167 are spaced from ceramic transducer elements 150 and 160, respectively, by liquid layers 174 and 176 of a thickness selected to facilitate ultrasonic pressure wave transmission.

Figure 3:
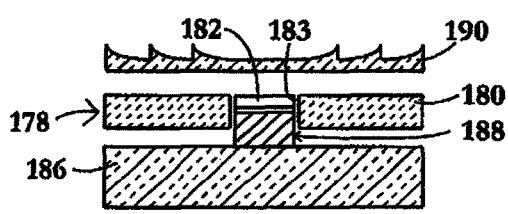
FIG. 3 is a schematic cross-sectional view of another dual mode transducer assembly in accordance with the present invention, showing a backing layer.

As shown in FIG. 3, in another modification of dual mode ultrasound transducer 148 of FIG. 9, a dual mode ultrasound transducer assembly or device 178 has a single piezoelectric ceramic transducer element 180 that serves in part as a substrate to a piezoelectric polymeric transducer elements 182 disposed inside a hole 183 in the ceramic transducer element 180 on a front side thereof, facing away from a backing layer 186. An epoxy or solid metal plug 188 is also disposed in hole 183, on a rear side, facing backing layer 186. As discussed above with respect to ultrasound transducer 148 of FIG. 9, ceramic transducer element 180 and polymeric transducer element or elements 182 function in a therapeutic and an imaging operating mode, respectively. As above, an acoustic lens 190 may be provided on the front side of transducer 180 (which takes a planar form), opposite backing 186 for focusing at least the therapeutic ultrasonic pressure waves at a focal point (spherical lens) or along a focal line (cylindrical lens). Lens 190 may be a concave lens, a convex lens, a Fresnel lens, a Fresnel multilevel lens, or a Field Conjugate lens.

Figure 4:
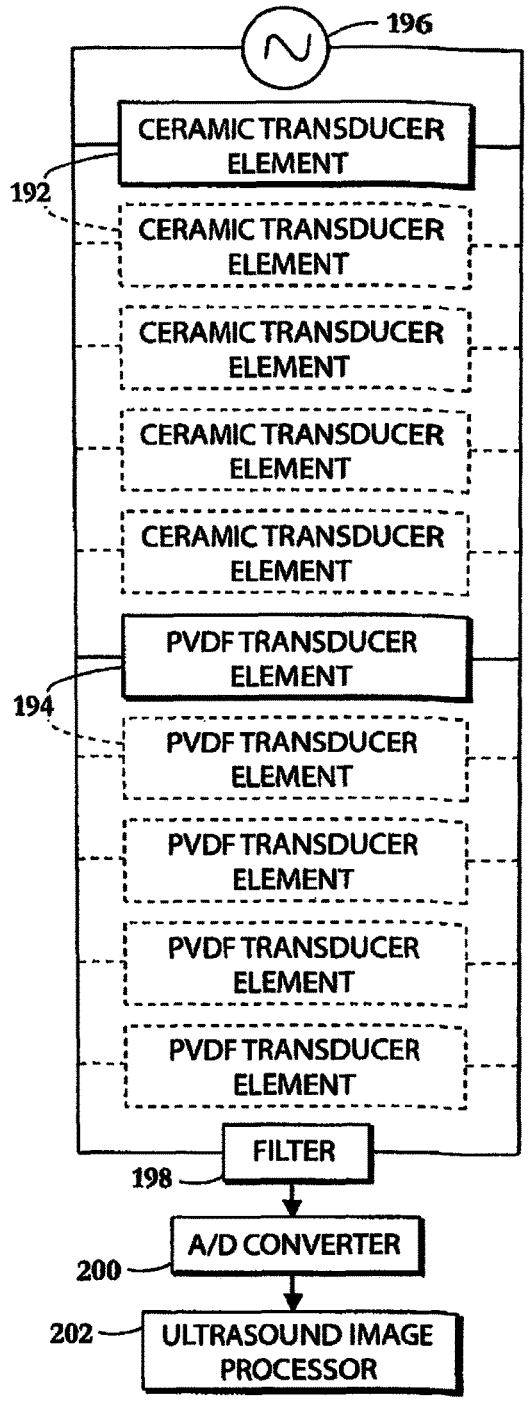
FIG. 4 is a circuit diagram incorporating a dual mode transducer, in accordance with the present invention.

FIG. 4 is a circuit diagram applicable to any of the dual mode piezocomposite transducers described herein. As shown in FIG. 12, one or more piezoelectric ceramic transducer elements 192 and one or more piezoelectric PVDF transducer elements 194 are connected in parallel to a source of high-intensity alternating voltage 196 and to a filter 198 having an output extending to an analog-to-digital converter 200 and from thence to an ultrasonic signal processor 202.

A relatively low driving voltage applied by source 196 to ceramic transducer elements 192 in a therapy mode does not engage PVDF transducer elements 194. PVDF transducer elements 194 have a substantially higher electrical impedance than the impedance of ceramic transducer elements 192 so that the total electrical impedance of the parallel circuit of FIG. 12 quite similar to that of ceramic, so that the presence of PVDF elements 194 in the circuit consequently has little effect on electrical power transfer and produced acoustic power. In an imaging mode, the low acoustic impedance of the PVDF transducer elements 194 provide broad band signals in response to received echoes due to the higher sensitivity of PVDF material relative to ceramic, while ceramic transducer elements 192 reflect most of the incoming acoustic energy due to high impedance contrast in an absence of acoustic matching layers.

Ceramic transducer elements 192 and polymeric transducer elements 194 can share the same electrodes or be connected to different electrodes. The number of individual therapeutic ceramic transducer elements 192 and imaging polymeric elements transducer elements 194 depends on the application.

If a PVDF transducer element 194 is used to send and receive acoustic signals as it is done in a standard pulse-echo imaging systems, then there is a need to couple that PVDF transducer to both a high-voltage excitation pulse generator (not separately shown) and the sensitive receiving electronics, i.e., ultrasonic signal processor 202. A transmit-receive (T/R) switching circuit (not shown) that would close during the application of a higher voltage signal but open while the probe is receiving acoustic echoes can be used. Alternatively, one may use a circuit designed to send acoustic signals using one or more piezoceramic transducer elements 192 and receive echoes with PVDF transducer elements 194. This is feasible, because of close packed interpenetrant nature of piezocomposite transducers disclosed herein and consequent negligible differences in beam directivity between ceramic and polymer elements.

Figure 5:
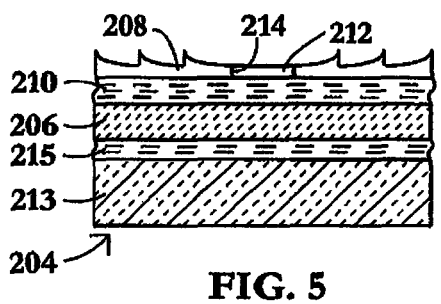
FIG. 5 is a schematic cross-sectional view of another dual mode transducer assembly in accordance with the present invention.

FIG. 5 depicts a dual mode transducer assembly 204 including a piezoceramic therapy transducer element 206 and an acoustic lens 208 spaced from one another by a liquid layer 210. Lens 208 is a Fresnel lens is provided in a central region with a piezoelectric polymeric imaging transducer element 212. Transducer element 212 occupies a through hole 214 in the lens. A backing layer 213 is paced by a liquid layer 215 from a back side of ceramic transducer element 206.

Figure 6:
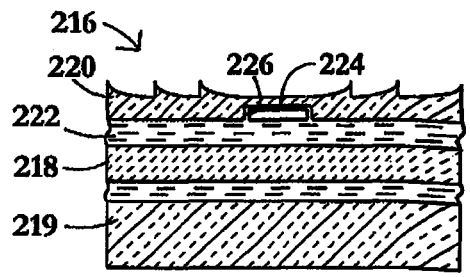
FIG. 6 is a schematic cross-sectional view of an alternate dual mode transducer assembly in accordance with the present invention.
Figure 13:
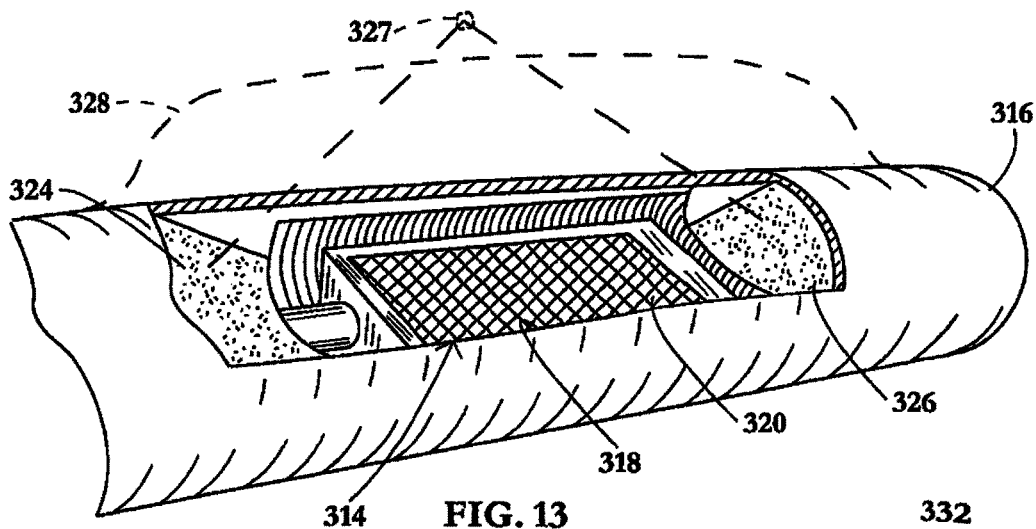
FIG. 13 is a schematic perspective or isometric view of a dual mode transducer assembly with two imaging transducer elements stationary relative to a casing, in accordance with the present invention.

FIG. 6 shows a modification 216 of the dual mode transducer assembly of FIG. 13. Dual mode transducer assembly 216 includes a piezoceramic therapy transducer element 218 and an acoustic lens 220 spaced from one another by a liquid layer 222. Lens 220 is provided in a central region with a piezoelectric polymeric imaging transducer element 224. Transducer element 224 is disposed in a recess 226 on a rear side of lens 220, facing ceramic transducer element 218 and a backing layer 219. Lens 220 may be a concave lens, a convex lens, a Fresnel lens, a Fresnel multilevel lens, or a Field Conjugate lens.

Backings 156, 166, 186, and backing layers (not illustrated) in dual mode transducer assemblies 204 and 216 of FIGS. 5 and 6 may be made of such a material as brass or SiC. Ceramic transducer elements 150, 160, 180, 206, and 218, as well as backings 156, 166, 186, and backing layers (not illustrated) in dual mode transducer assemblies 204 and 216 of FIGS. 5 and 6, are mounted to respective casings or holder members, as discussed below with reference to FIG. 7. Accordingly, it is to be understood that all transducers disclosed herein are typically provided as integrated parts of ultrasound probes, mounted inside liquid-filled bladders or boluses that in turn are disposed at least in part inside rigid probe casings.

Figure 7:
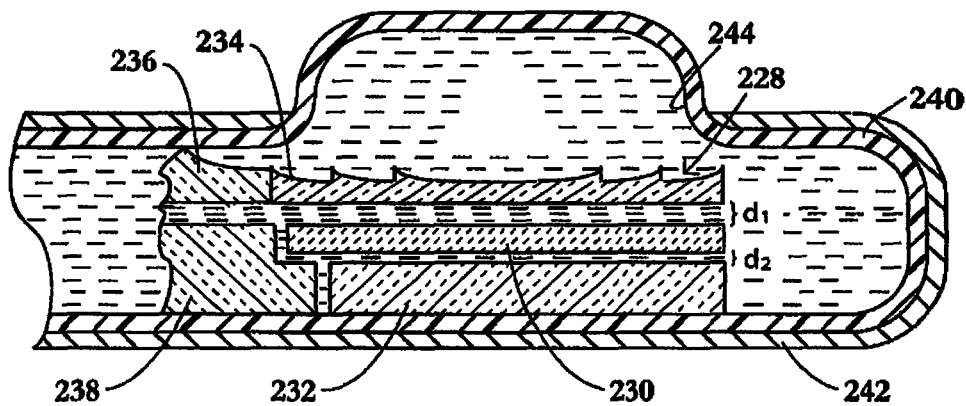
FIG. 7 is a is a schematic cross-sectional view of a transducer assembly or device having a Fresnel lens in accordance with the present invention, showing a holder for the transducer and lens assembly.

As illustrated in FIG. 7, an ultrasound transducer assembly 228 includes a planar piezoceramic therapy transducer element 230, a backing 232, and an acoustic lens 234 (e.g., a concave lens, a convex lens, a Fresnel lens, a Fresnel multilevel lens, or a Field Conjugate lens) that are connected to one or more mounting members 236, 238 and disposed inside a flexible bladder 240 that is in turn disposed inside a casing 242 provided with a window 244. Casing 242 and the contents thereof comprise a probe for high-intensity focused ultrasound (HEM) surgical therapy.

Lens 234 is spaced from transducer element 230 by a distance $d_1$ equal to $(2n-1)\lambda/4$ where n is a non-negative integer and $\lambda$ is the wavelength of the ultrasonic pressure waves for therapeutic applications. Transducer element 230 is spaced from backing 232 by a distance $d_2$ equal to $n\lambda/2$ where again n is a non-negative integer and $\lambda$ is the wavelength of the ultrasonic pressure waves for therapeutic applications.

Figure 8:
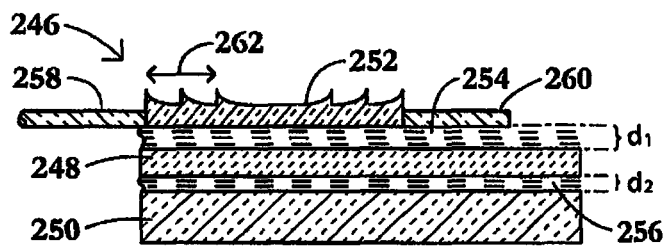
FIG. 8 is a schematic cross-sectional view of a transducer assembly with a relatively shiftable Fresnel lens, in accordance with the present invention.

As depicted in FIG. 8, an ultrasound transducer assembly 246 at least for use in a therapy mode comprises a planar piezoceramic transducer element 248, a backing layer 250, and an acoustic lens 252 (a concave lens, a convex lens, a Fresnel lens, a Fresnel multilevel lens, or a Field Conjugate lens) aligned with one another and spaced by liquid-filled gaps 254 and 256 of thickness $d_1$ and $d_2$, respectively. Two metal plates 258 and 260, which serve to block ultrasonic wave transmission, are connected to lens 252 on opposing sides thereof. Lens 252, together with metal blockers 258 and 260, is longitudinally shiftable alternately in opposite directions, as indicated by double headed arrow 262, relative to transducer element 248 for enabling a user to move a focal zone of the ceramic transducer. Lens 252 may be a cylindrical lens, in which case the focal zone or locus (set of points) is a line. Moving the lens 252 relative to the transducer 248 (and probe casing, not shown) shifts the focal locus along a plane parallel to the transducer and thus parallel to an organ surface against which the therapy probe lies. Metal blockers 258, 260 prevent ultrasonic pressure waves from radiating into the patient except towards the focal locus defined in part by lens 252. Any of the lenses disclosed herein may be movably mounted relative to the respective ceramic transducer element to facilitate application of focused high-intensity ultrasound to an extended target site.

FIG. 9 depicts a dual mode transducer assembly 264 with a rotatable holder 266, as indicated by an arrow 268. Holder 266 includes a head 270 in the form of a right rectangular prism. Head 270 is provided on one face 272 with at least one high-power ceramic transducer element 274 that is either planar or shaped for focusing. In the case of a planar transducer element 274, an acoustic lens (not shown) is provided for focusing the planar ultrasonic waves from transducer onto a focal locus such as a point (spherical lens) or a line (cylindrical lens). Another face 276 of head 270 carries at least one planar or focally shaped piezoelectric polymeric (e.g., PVDF) transducer element 278. In the case of a planar transducer element 278, an acoustic lens (not shown) may be provided for focusing the planar ultrasonic waves from a focal locus onto transducer element 278. Where the ultrasonic pressure waves generated by ceramic transducer element 274 for therapy have a frequency that is substantially different than the frequency of pressure waves for imaging, two different lenses may be provided. The lens may be shiftably mounted to a probe casing (not shown) for alternate use during therapy and imaging operations.

As in the case of other transducer devices described above, the dual mode transducer assembly 264 of FIG. 9 is typically incorporated into an ultrasound probe including a casing and bolus. More particularly, holder 266 is disposed inside a liquid-filled bladed or bolus (not shown) that in turn is disposed inside a probe casing (not shown) in juxtaposition to a window in the probe casing. As discussed above, transducer elements 274 and 278 are used in alternation in therapeutic and imaging operating modes, respectively. Holder 266 is rotated in order to juxtapose transducer element 274 to the casing window during a period of therapy application and subsequently to juxtapose transducer element(s) 278 to the casing window during an imaging interval.

FIG. 10 depicts a modification 280 of the dual mode transducer assembly 264 of FIG. 9 and uses the same reference numerals to designate the same parts. In transducer assembly 280, ceramic transducer element 274 and polymeric transducer element 278 are located in adjacent faces 272 and 282, rather than opposite faces 272 and 276 as in transducer assembly 264 of FIG. 9. Accordingly, the operation is slightly altered inasmuch as holder 266 need be rotated only 90° rather than 180° to change from therapy mode to imaging mode and vice versa.

As shown in FIG. 11, a dual mode transducer assembly 284 has a longitudinally reciprocatable holder 286, as indicated by a double-headed arrow 288. Holder 286 includes a head 290 in the form of a right rectangular prism or plate. Head 290 is provided on one face 292 with both a planar or shaped high-power ceramic transducer element 294 and a planar or shaped piezoelectric polymeric (e.g., PVDF) transducer element 296. In the case that transducer elements 294 and/or 296 are planar, one or more acoustic lenses (not shown) may be provided for focusing purposes. Again, holder 286 is disposed inside a liquid-filled bladed or bolus (not shown) that in turn is disposed inside a probe casing (not shown) in juxtaposition to a window 298 in the probe casing. Transducer elements 294 and 296 are alternately juxtaposed to the casing window 298 to implement therapeutic and imaging operating modes, respectively, by shifting holder 286 in a distal or proximal direction as appropriate.

FIG. 12 shows a dual mode transducer assembly 300 including a probe casing 302 provided at a distal end with a window 304 in a sidewall (not separately designated) and further including a piezoceramic transducer element 306 in a holder 308 disposed inside the casing. A piezoelectric polymeric imaging transducer element 310 is disposed in window 304, on an outer side or surface of casing 302, and located along an arcuate bridge (not separately designated) so as to bifurcate the window. Portions of window 304 are located on opposite sides of the bridge and imaging transducer element 310, where the bridge extends from one longitudinal side of window 304 town opposite longitudinal side or edge thereof. A bolus or bladder member 312 is provided outside of casing 302 and may be pressurized to expand from a partially inflated storage configuration (not shown) to a fully inflated use configuration as shown.

FIG. 13 illustrates a dual mode transducer assembly 314 including a probe casing 316 provided in a sidewall (not separately designated) at a distal end with a window 318. A planar or focally shaped piezoceramic transducer element 320 is disposed on a holder 322 inside casing 316. Two piezoelectric polymeric imaging transducer elements 324 and 326, disposed in fixed or stationary positions on an outer side or surface of casing 316 along distal and proximal sides of window 318 at inclined angles relative to an outer or exterior surface (not separately designated) of casing 316 and located inwardly from that outer or exterior surface, are configured for scanning tissues at a focal zone 327. A bolus or bladder member 328 is provided outside of casing 316 and may be pressurized to expand from a partially inflated storage configuration (not shown) to a more expanded use configuration as indicated.

Figure 14:
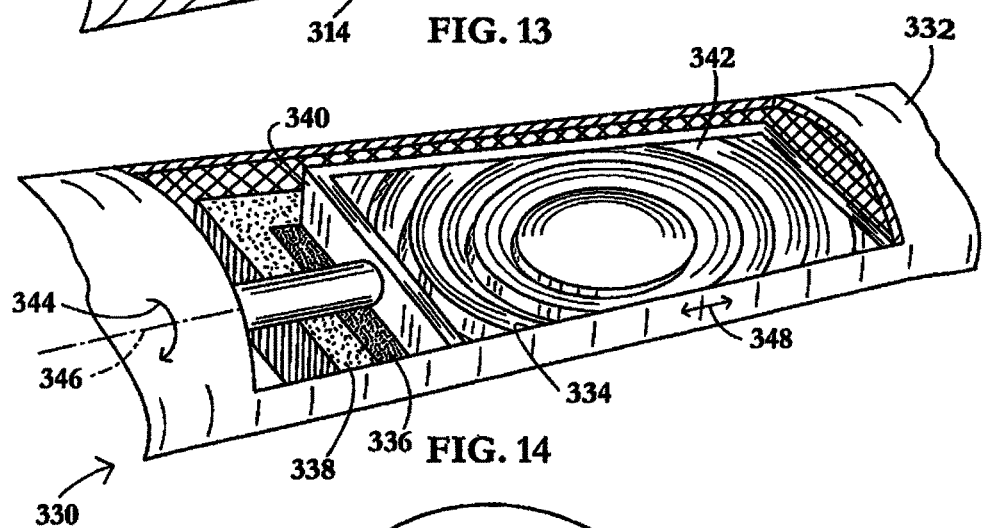
FIG. 14 is a schematic partial perspective or isometric view of a transducer assembly with a tiltable and longitudinally positionable spherical Fresnel lens, in accordance with the present invention.
Figure 15:
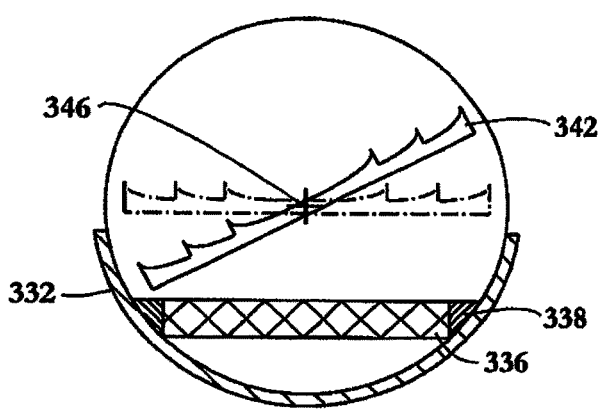
FIG. 15 is a schematic transverse cross-sectional view of the transducer assembly of FIG. 22.

Pursuant to FIGS. 14 and 15, an ultrasound transducer assembly 330 includes a probe casing 332 provided in a sidewall (not separately designated) at a distal end with a window 334. A piezoceramic transducer element 336 is disposed on a holder 338 inside casing 332. Also disposed on a holder 340 inside casing 332 is a spherical acoustic Fresnel lens 342. As indicated by an arrow 344 in FIG. 15, holder 340 and Fresnel lens 342 are rotatable about a longitudinal axis 346, whereby a focal point of the lens moves along an arc. In addition, holder 340 and lens 242 may be longitudinally reciprocatable, as indicated by a double-headed arrow 348, so that the focal point of the lens may be moved distally and proximally. A bolus or liquid-filled bladder (not shown) is provided about the casing 332.

Lens 342 may be flanked by metal plates (not shown) for limiting ultrasound irradiation.

As depicted in FIGS. 16 and 17, an ultrasound transducer assembly 350 includes a high-power therapy transducer 352 in a parabolic or cylindrical configuration, on a holder 354 inside a probe casing 356. Transducer element 352 is disposed so that its axis extends in a distal-proximal direction, parallel to a longitudinal axis 358 of the probe casing. Ultrasound transducer assembly or probe 350 further includes a cylindrical acoustic Fresnel lens 360 that is oriented with its axis transverse to the axis of transducer element 352, thereby producing a focal zone or locus that is a point. As indicated, lens 360 may be rotatable and optionally longitudinally shiftable, for shifting the location of the focal point relative to the probe and accordingly relative to a patient.

Polymeric piezoelectric materials suitable for imaging transducer elements 152, 162, 182, 212, 194, 224, 278, 296, 310, 324, and 326 include polyvinylidene fluoride (PVDF), and copolymers of PVDF such as trifluoroethylene (TrFE) with a piezoelectric voltage constant $g_{33} > 100 \times 10^{-3}$ Vm/N. Piezoceramic materials suitable for therapy transducer elements 150, 160, 180, 206, 192, 218, 230, 248, 274, 294, 306, 320, and 336 include modifications of $BaTiO_3$, $Pb(Ti,Zr)O_3$ (PZT) and $PbNb_2O_6$ ceramics with a high piezoelectric strain constant, $d_{33} > 200 \times 10^{-12}$ m/V.

Imaging transducer elements as used herein are derived from an appreciation of the properties of polyvinylidene fluoride (PVDF). That polymer is a semi-crystalline, thermoplastic fluoroplastic. It has received a considerable research attention in past decades that stems from the discovery of its piezoelectric and pyroelectric properties and its subsequent application as an electret and piezoelectric transducer. With its low acoustic impedance of 3.5 MRyals and high voltage constant PVDF makes an ideal ultrasound receiver and shows definite advantages over ceramic counterparts. As a transmitter of acoustic power, the PVDF transducer is quite poor, but its enhanced sensitivity on reception provides a send-receive factor comparable to that of ceramic. The table below summarized common applications and lists relevant piezoelectric properties for typical piezoelectric ceramic, quartz and PVDF.

Piezoelectric material properties (Gallentree, 1983, Review of Transducer Applications of Polyvinylidene Fluoride, *Piezoelectricity*, Key Paper in Physics, 189-194; Kino, 1987, Acoustic Waves: Devices, Imaging, and Analog Signal Processing, Prentice Hall, Englewood Cliffs, NJ, Appendix B; Mason, 1966, Physical Acoustics: Principles and Methods, edit Rosenberg, Mir, Moscow)

|  | Applications | Curie T, ° C. | $Q_m$ | $d_{33}$, m/V $10^{-12}$ | $g_{33}$, Vm/N $10^{-3}$ |
|---|---|---|---|---|---|
| Navy Type I (PZT4) | STM, nanopositioning, medical therapeutics. | 328 | 500 | 289 | 25 |
| Navy Type II (PZT5A) | flow and level sensing and medical Doppler transducers | 365 | 75 | 374 | 25 |
| Navy Type III (PZT8) | Ultrasonic cleaners, cell disruption, phacoemulsification, and high power ultrasonics | 300 | 1000 | 225 | 25 |
| Navy Type VI (PZT5H) | Medical diagnostics, industrial NDT, STM/AFM, and nano-Positioning | 193 | 65 | 593 | 20 |
| PVDF | Insulation (Kynar ®), key boards, sonar hydrophones, pulse-echo ultrasonic transducers | 100 | 13 | 20 | 210 |
| Quartz | crystal clock oscillator, mass microbalance, and thin-film thickness monitoring | — | 25000 | 2 | 50 |

A typical PVDF transducer does not require cumbersome acoustic matching layers, inherent in ceramic transducers, and is relatively easy to produce in a variety of forms and may be press fit into a curved shape.

Polymeric imaging transducer elements 152, 162, 182, 212, 224, 278,296 310, 324, and 326 are operatively connected to ultrasound image processor 202 or other appropriate waveform processing and digital image generation apparatus, as well known in the art. Ceramic therapy transducers 150, 160, 180, 206, 192, 218, 230, 248, 274, 294, 306, 320, and 336 may operate in part to generate outgoing scanning waveforms. Where there are moving parts, such as lenses moving relative to therapy transducers, the motion may be implemented via electric motors, stepper motors, linear motors, etc., and the motion may be monitored by feedback sensors such as encoders, voltage dividers, etc.

Ceramic transducer elements 150, 160, 180, 206, 192, 218, 230, 248, 274, 294, 306, 320, and 336 function in a therapy mode of operation of the respective transducer assembly or device to generate high-power ultrasonic pressure waves, in response to a suitable energizing signal, that are transmitted into a patient for implementing or assisting in a surgical operation such as thermal ablation, hyperthermia, transfection and/or drug delivery. Polymeric transducer elements 152, 162, 182, 212, 224, 278,296 310, 324, and 326 function in a diagnostic or scanning mode of operation of the respective transducer assembly or device to detect incoming ultrasonic pressure waves that are reflected from internal tissue structures of a patient in response to a suitable scanning wave. As discussed above with reference to FIG. 4, the therapeutic ceramic transducer elements and the diagnostic polymeric transducer element may be connected in parallel in the same circuit.

Thus, the ultrasound transducer devices described herein are provided with electrical contacts (not shown) enabling a connection of the respective ceramic transducer elements 150, 160, 180, 206, 192, 218, 230, 248, 274, 294, 306, 320, and 336 in operative circuits for generating, for example, high-intensity focused ultrasound and enabling a connection of the respective polymeric transducer elements 152, 162, 182, 212, 224, 278,296 310, 324, and 326 in operative circuits for scanning organic tissues to generate ultrasonic scan data for analysis and processing into images.

FIG. 18 depicts a Fresnel lens 402 that is reciprocatable along a given direction, as indicated by a double-headed arrow 404, in parallel to a planar front radiating face 406 of a flat transducer element 408. Lens 402 is spaced from front face 406 of transducer element 408 by a gap 409 of a thickness $(2n+1)\lambda/4$ where n is a non-negative integer and $\lambda$ is the wavelength of the ultrasonic pressure waves for therapeutic applications. Transducer element 408 is spaced from a backing (not shown) by a distance $n\lambda/2$ where again n is a non-negative integer and $\lambda$ is the wavelength of the ultrasonic pressure waves for therapeutic applications.

Figure 19C:
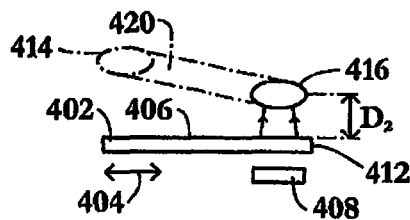

Lens 402 is configured to have a focal length that varies in a continuous gradient from a maximum focal length $f_1$ at one end 410 of the lens to a minimum length $f_2$ at an opposite end 412 of the lens. As depicted in FIG. 19A, a focal zone 414 is disposed at a maximum distance $D_1$ (approximately length $f_1$) from lens 402 when transducer element 408 is aligned with the first end 410 of the lens. When transducer element 408 is aligned with the opposite end 412 of lens 408, ultrasound waves converge at a focal zone 416 located at a minimum distance $D_2$ (approximately length $f_2$) from lens 402, as shown in FIG. 19C. When transducer element 408 is aligned with a middle region of lens 408 as shown in FIG. 19B, ultrasonic pressure waves generated in a subject converge at a focal zone 418 disposed at an intermediate distance $D_3$ from lens 402. Accordingly, by moving lens 402 in the direction of arrow 404 one focuses destructive ultrasound energy at target regions or focal zones 414, 416, 418 located at different depths $D_1$, $D_2$, $D_3$ in the patient and at different laterally staggered positions along a skin or internal surface. As indicated in FIG. 19C, generation of ultrasound energy by transducer element 408 while lens is moving from right to left relative to the transducer can produce a continuous elongate region 420 of therapeutically damaged tissue.

Figure 20:
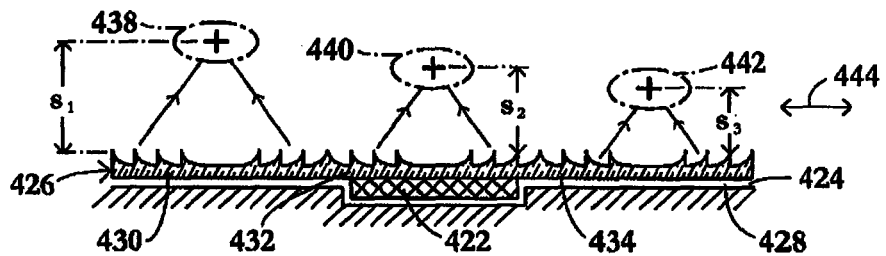
FIG. 20 is schematic cross-sectional view of another ultrasound transducer assembly in accordance with the present invention, including a transducer element and a Fresnel lens having a plurality of discrete sections of different focal lengths.

FIG. 20 shows a transducer element 422 ensconced in a backing layer 424 and spaced from a Fresnel lens 426 by a liquid-filled gap 428 of thickness $(2n+1)\lambda/4$ where n is a non-negative integer and $\lambda$ is the wavelength of the ultrasonic pressure waves for therapeutic applications. Lens 426 comprises a plurality of adjacent sections 430, 432, 434 each of a respective focal length $s_1$, $s_2$, $s_3$. Focal lengths $S_1$, $s_2$, $s_3$ are shown to vary in a monotonically decreasing sequence. However, any arrangement of any practicable number of sections of different focal lengths may be made.

The distance (generally $s_1$, $s_2$, $s_3$) of a target tissue mass or focal zone 438, 440, 442 from lens 426 varies in accordance with which lens section 430, 432, 434 is in alignment with transducer element 422. In addition, limited lateral motion of lens 426 (see arrow 444) relative to transducer 422 while any given lens section 430, 432, 434 remains in alignment with transducer element 422 will shift the respective focal zone 438, 440, 442 laterally in parallel to lens 426 and transducer element 422 (assuming planar configurations of both).

Figure 21:
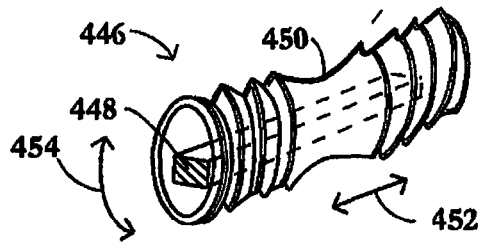
FIG. 21 is a schematic perspective view of yet a further ultrasound transducer assembly in accordance with the present invention, including a transducer element and a generally cylindrical Fresnel lens element having a focal length that varies in a continuous gradient around a circumference of the lens.

As illustrated in FIG. 21, an ultrasound transducer assembly 446 includes a transducer element 448 on a holder (not separately illustrated) disposed inside a generally cylindrical or tubular Fresnel lens 450 which has a focal length that varies in a continuous gradient (or, alternatively, in discrete steps) around the circumference of the lens. Thus rotating lens 450 relative to transducer element 448, as indicated by an arrow 454, enables one to target a tissue mass at a controllably variable depth or distance from assembly 446. Shifting lens 450 longitudinally (arrow 452) relative to transducer element 448 enables one to vary the position of the focal zone or target tissue region in the direction of arrow 452.

Figure 23:
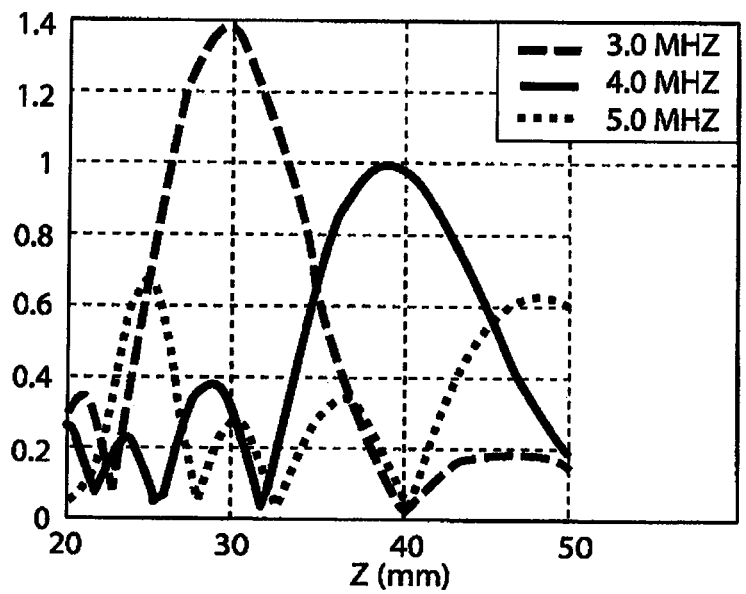
FIG. 23 is a graph of focusing effectiveness as a function of distance from a 4-zone 4 MHz Fresnel lens as a function of three acoustic frequencies.
Figure 24:
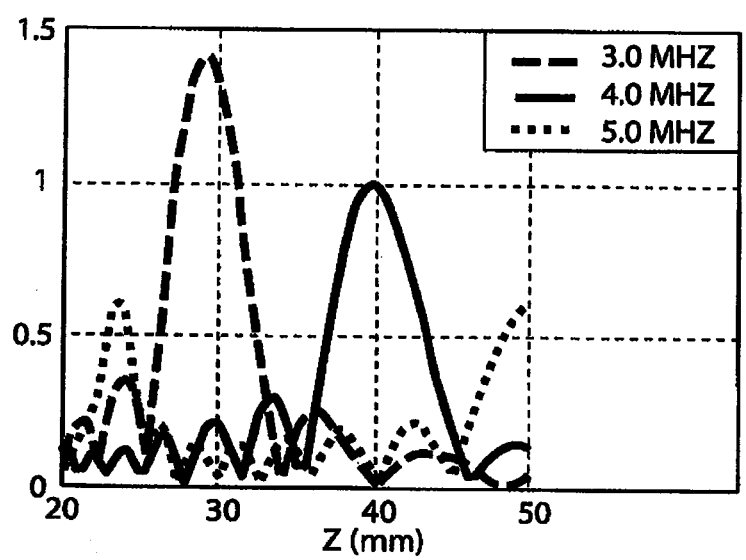
FIG. 24 is a graph of focusing effectiveness as a function of distance from an 8-zone 4 MHz Fresnel lens as a function of three acoustic frequencies.

The depth of focus can be controlled by adjusting the transducer operating frequency. In the latter case, the Fresnel lens changes its depth of focus depending on the frequency thus offering an elegant way of controlling energy deposition at different depths when treating large tissue volumes using a single fixed lens and a set of high-power transducers capable of operating at a range, or with a discrete set, of frequencies. FIGS. 23-24 shows relative intensity profiles created by a 2-zone Fresnel lens, a 4-zone Fresnel lens and an 8-zone Fresnel lens at a set of three frequencies. The 8-zone lens of FIG. 24 was designed to focus 4 MHz waves at 40 mm depth. Clearly, the use of a 5 MHz frequency moves the focal zone deeper, outward by about 10 mm, while the focal spot is brought to a shallower depth at an operating frequency of 3 MHz. The transducer is moved relative to a lens or both are moved relative to a probe in order to achieve large volume tissue impact.

Figure 25:
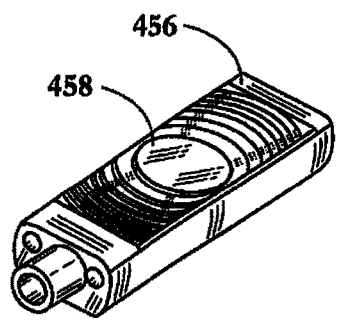
FIG. 25 is a perspective view of a flat-pack HIFU head assembly in accordance with the present invention.
Figure 26:
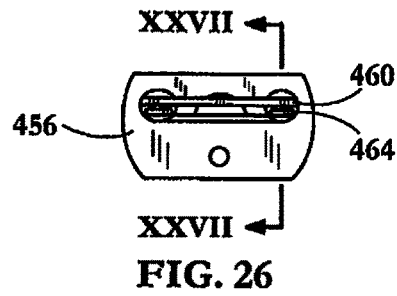
FIG. 26 is an end elevational view of the HIFU head assembly of FIG. 25.
Figure 27:
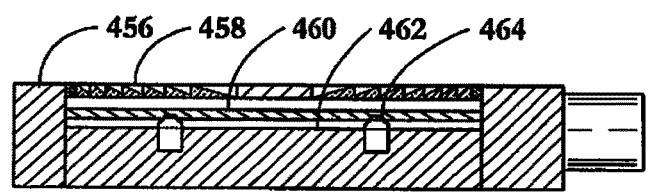
FIG. 27 is a longitudinal cross-sectional view taken along line XXVII-XXVII in FIG. 26.

FIGS. 25-27 are a particular configuration of a probe head of a HIFU treatment device showing a housing 456, a Fresnel lens 458, a rectangular piezoelectric transducer 460, a reflector 462, and mill-max spring-loaded pins 464.

Figure 28:
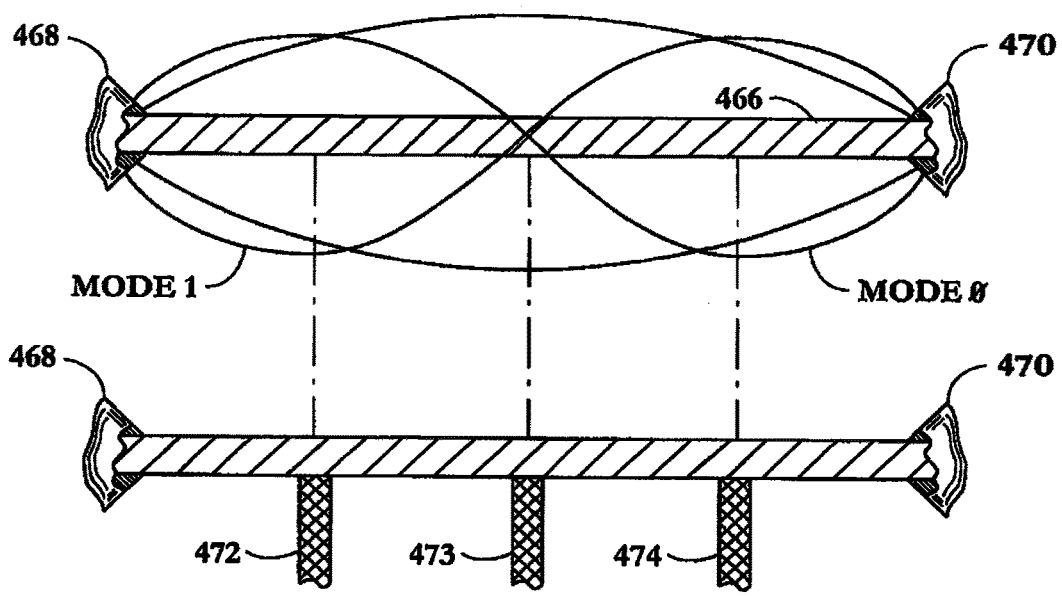
FIG. 28 is a schematic cross-sectional view of a piezoelectric transducer showing vibration modes at the top and metal supports or electrodes at the bottom for damping modes of vibration.

FIG. 28 shows a planar piezoelectric transducer element 466 affixed at opposite ends 468 and 470 to a housing or frame (not shown) and provided with three metal supports 472-474, optionally in the form of electrodes. Supports 472 and 472 are positioned at the nodes of vibration mode 1, while support 473 is positioned at the node of vibration mode 0. FIGS. 29 and 30 depict a HIFU transducer assembly or device including a cylindrical transducer element 476 operating in wall thickness mode and an essentially cylindrical Fresnel lens 478 having an azimuthally variable focal length, the transducer element being located inside the lens. FIG. 30 shows a variable-depth focal zone 480 about the lens 478.

Figure 22:
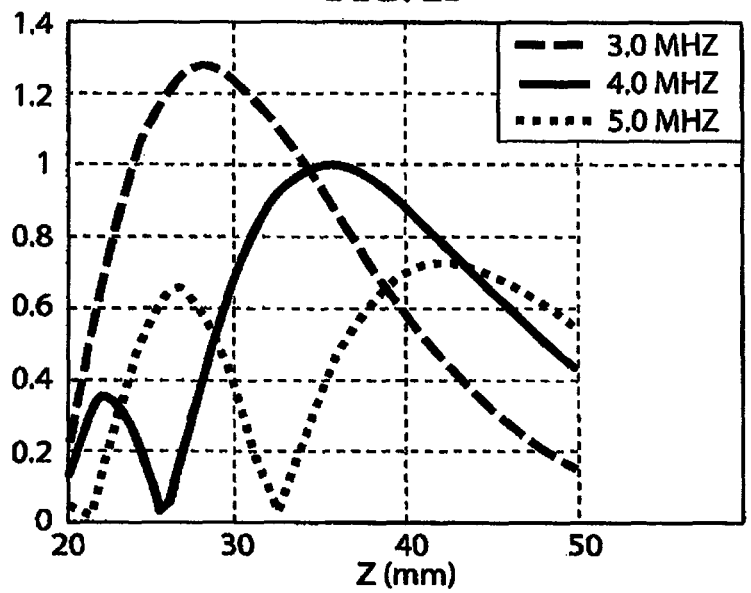
FIG. 22 is a graph of focusing effectiveness as a function of distance from a 2-zone 4 MHz Fresnel lens as a function of three acoustic frequencies.

FIG. 31 shows a lens L constructed to focus planar acoustic waves of frequency $f_1$ at a focal point $F_1$. The line Ψ constitutes a construction line. The solid arcs with the center of origin $F_1$ are the phase fronts spaced apart by one wavelength $\lambda_1$ from each other. The first solid circle is tangent to the line Ψ not shown. The intersection of solid circles with line Ψ marks the location of the respective Fresnel zones. At a higher frequency $f_2$ the acoustic wavelength becomes smaller: $\lambda_2 < \lambda_1$. If lens L design is fixed, passing a higher frequency waves through lens L is similar to having the phase circles spaced apart by a smaller distance $\lambda_2$, shown by dashed arcs. In order to focus the dashed arcs, which correspond to frequency $f_2 > f_1$, must intersect the line Ψ at the same points as solid arcs, which correspond to the original lens frequency $f_1$. Clearly, on average dashed arcs can intersect line Ψ at the same points if their center of origin $F_2$ is located farther away from the line Ψ than $F_1$. Using this geometrical construction and neglecting terms of the second order in wavelength an approximate formulae that related the focal depth of a lens and operating frequency is: $F=F_1 f_1/f_2$. This equation predicts the focal distances for the relatively small number of the Fresnel zones and for the cases where wavelength is much smaller than focal distances F. For example, going from 4 MHz to 5 MHz would result in a shift of the focal spot from 35 mm to approximately 43 mm, in good agreement with FIG. 22 field simulation results. Thus, the higher frequency will focus deeper and, respectively, lower frequency will focus at shallower depth than original frequency.

By constructing a lens made of relatively soft silicone, like RTV rubber, one can achieve the limited field transformation effects without changing frequency of transducers. For example, simulation shows that 30% stretch in one direction results in a field blurring and slight depth decrease. This effect can be used to control the volume of ultrasonic energy deposited by a transducer and focused by deformable lens. There is a potential to ablate larger tissue volume with a field that is less focused, yet has sufficient intensity. Stretching the lens is a simple and controllable process that will enable blurring of the focal intensity zone over larger volume, which can be beneficial for large tumor ablations.

Figure 32:
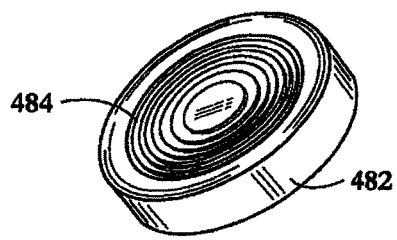
FIG. 32 is a schematic perspective view of another flat-pack HIFU head assembly in accordance with the present invention.
Figure 33:
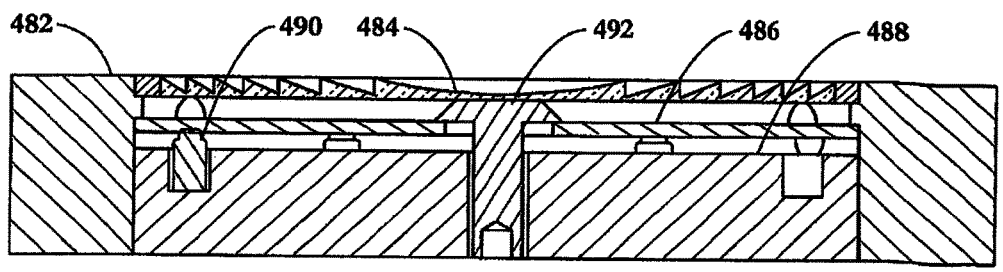
FIG. 33 is a cross-sectional view of the assembly of FIG. 32.

FIGS. 32 and 33 show a flat circular configuration for a probe head of a HIFU treatment device, including a housing 482, a Fresnel lens 484, a rectangular piezoelectric transducer 486, a reflector 488, mill-max spring-loaded pins 490, and a center electrode 492.

Figure 34:
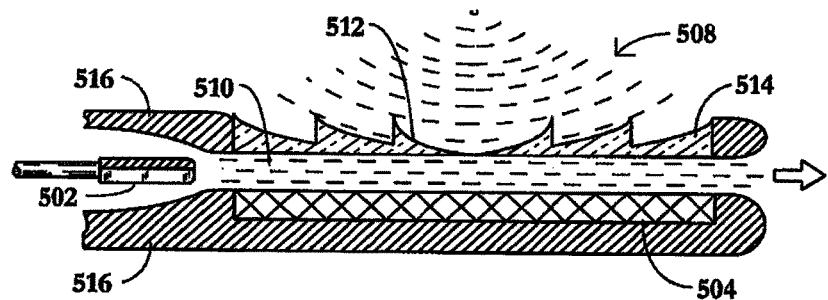
FIG. 34 is a schematic cross-sectional view of another transducer assembly in accordance with the present invention, showing an imaging transducer disposed at an inactive position relative to a focusing lens.
Figure 35:
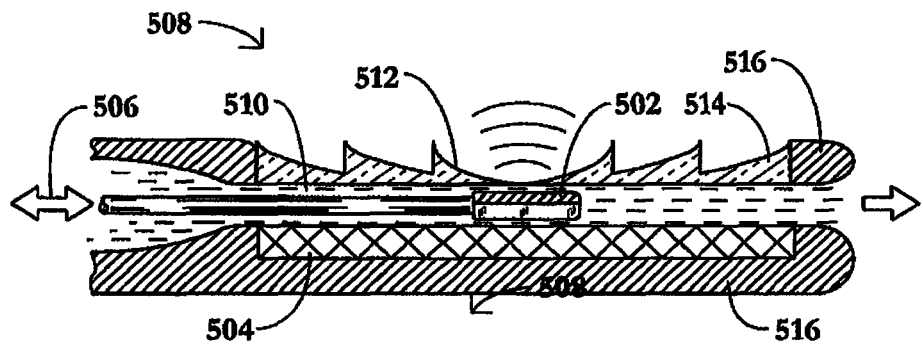
FIG. 35 is a schematic cross-sectional view of the transducer assembly of FIG. 34, showing the imaging transducer disposed at an active location aligned with a central region of the focusing lens.

Another aspect of the present invention, depicted in FIGS. 34 and 35, includes an ultrasound imaging transducer or transducer array 502 movable relative to a therapeutic transducer element or array 504 to thereby obtain an image of a region exposed to high power ultrasound generated by the therapeutic transducer element or array and ensure a controlled and safe therapy process. The movability of imaging transducer or transducer array 502, as represented by double headed arrow 506 in FIG. 35, facilitates the application of the high power ultrasonic energy to an extended surgical target region.

As shown in FIGS. 34 and 35, therapeutic transducer element or array 504 takes a planar form and a Fresnel focusing lens 508 is held by a casing or frame 516 in position parallel to element or array 504, separated by small water gap 510. The water or other suitable liquid in gap 510 facilitates the cooling of therapeutic transducer element or array 504 and serves as a pathway for the introduction of imaging transducer or probe 502.

Imaging transducer or array 502 may constitute a thin plate not exceeding in thickness the width of gap 510 between therapy transducer 504 and lens 508 and having transverse dimensions comparable to a first or innermost or central Fresnel zone 512 of the lens. Fresnel zone 512 is the thinnest part of lens 508 and enables efficient and lossless transmission and reception of ultrasound by imaging transducer 502, when that transducer element or array is positioned in alignment with the central or innermost Fresnel zone 512 as depicted in FIG. 35.

Imaging transducer 502 may contain several layers of acoustical matching layers, active piezo-materials, bonding and backing layers, constituting a stacked design, or made of piezo-composite material, which can contain a single or plurality of discretely imprinted electrodes that provide for a single element probe or imaging phased array configuration, thus enabling imaging at variable focal depths.

The middle section of Fresnel lens zone 512 is thinner than an outermost section 514 that has the minimum thickness:

$$d \geq \frac{1}{f\left(\frac{1}{c_w} - \frac{1}{c_m}\right)},$$

where $c_w$ and $c_m$ are the sound speed in water and lens material, respectively, and f is the frequency. Thus innermost or central Fresnel section or zone 512 enables most of the transmission.

Figure 36:
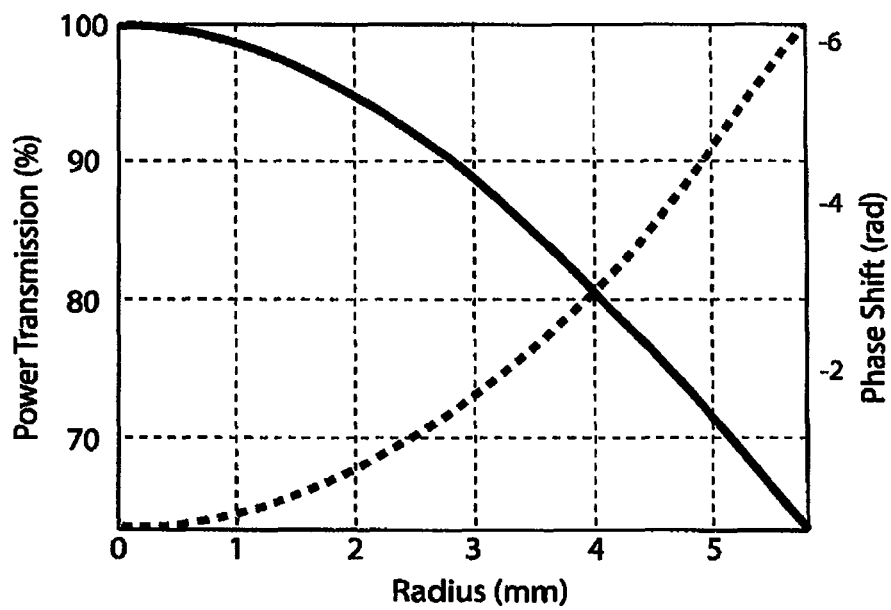
FIG. 36 is a pair of graphs, the first graph showing power transmission through a Fresnel lens as a function of radius, the second graph showing phase shift as a function of radius.

For example a 4 MHz lens with a nominal focal depth of 45 mm has a first or innermost Fresnel zone of about 11 mm in diameter. As shown in FIG. 36, the relative power transmission (solid line, left axis) as a function of radius varies from 100% in the middle to less than 70% in the outer section, assuming first order polystyrene lens. At the same time, the outer section or zone produces a larger phase shift (dashed line, right axis) for the propagating ultrasound waves, which is important for focusing, while middle section introduces minimal phase shift to propagating waves. Thus, it is feasible to replace the middle or innermost section with an opening of about 6 mm diameter, which is sufficient to provide an imaging window for a movable imaging transducer. Alternatively, an imaging transducer made of low ultrasound absorption piezo-polymer material can be an integral part of a movable and variable focal distances lens, as disclosed above, to enable simultaneous focusing and imaging at different distances, which is required for a controllable, effective and safe ultrasound ablation performed under ultrasound imaging guidance.

The invention claimed is:

1. An ultrasonic diagnostic and treatment probe comprising:
    a casing provided at a distal end with a sidewall having a window;
    a transducer holder disposed inside said casing so as to be movable relative to said window;
    at least one therapeutic transducer element made of a piezoelectric ceramic and mounted to said holder so as to be juxtaposable to said window; and
    at least two imaging transducer elements made of a piezoelectric polymeric material and fixed to an outer or exterior surface of said casing on distal and proximal sides of said window respectively, said at least two imaging transducer elements being stationary with respect to said casing, said at least two imaging transducer elements being separate and different from said at least one therapeutic transducer element, said at least two imaging transducer elements being configured so as to be utilizable for only imaging and said at least one therapeutic transducer element being configured so as to be utilizable for only therapy,
    wherein said casing has an outer or exterior surface, said two imaging transducer elements being located inwardly from said outer or exterior surface and disposed at inclined angles relative to said outer or exterior surface of said casing.

2. The probe defined in claim 1 wherein said holder is provided with a plurality of faces, said holder being rotatably mounted in said casing so that different ones of said faces may be alternately positioned adjacent to and facing said window, said at least one therapeutic transducer element being provided on a first one of said faces.

3. The probe defined in claim 2 wherein said first one of said faces is oriented at a non-zero angle relative to said second one of said faces.

4. The probe defined in claim 1 wherein said casing has a first longitudinal axis and said holder has a second longitudinal axis extending parallel to said first longitudinal axis, said at least one therapeutic transducer element being disposed along a side of said holder, said holder being longitudinally reciprocatable relative to said casing so that said at least one therapeutic transducer element is alternatively disposable adjacent said window.

5. The probe defined in claim 1, further comprising an acoustic focusing lens mounted at least indirectly to said casing adjacent to said window.

6. The probe defined in claim 1 wherein said two imaging transducer elements are fixed to said casing adjacent said window.

7. An ultrasonic diagnostic and treatment probe comprising:
    a casing provided at a distal end with a sidewall having a window;
    a transducer holder disposed inside said casing so as to be movable relative to said window;
    at least one therapeutic transducer element made of a piezoelectric ceramic and mounted to said holder so as to be juxtaposable to said window;
    at least one imaging transducer element made of a piezoelectric polymeric material and fixed to an outer or exterior or surface of said casing in a region about said window, said at least one imaging transducer element being stationary with respect to said casing, said at least one imaging transducer element being separate and different from said at least one therapeutic transducer element, said at least one imaging transducer element being configured so as to be utilizable for only imaging and said at least one therapeutic transducer element being configured so as to be utilizable for only therapy; and
    a bolus or bladder member provided outside of said casing and surrounding said window and said at least one imaging transducer element,
    wherein said casing has an outer or exterior surface, said two imaging transducer elements being located inwardly from said outer or exterior surface and disposed at inclined angles relative to said outer or exterior surface of said casing.

8. An ultrasonic diagnostic and treatment probe comprising:
    a casing provided at a distal end with a sidewall having a window;
    a transducer holder disposed inside said casing so as to be movable relative to said window;
    at least one therapeutic transducer element made of a piezoelectric ceramic and mounted to said holder so as to be juxtaposable to said window; and at least two imaging transducer elements made of a piezoelectric polymeric material, said at least two imaging transducer elements being fixed to an outer or exterior surface of said casing and stationary with respect to said casing, said at least two imaging transducer elements being disposed on distal and proximal sides of said window respectively, said at least two imaging transducer elements being separate and different from said at least one therapeutic transducer element, said at least two imaging transducer elements being configured so as to be utilizable for only imaging and said at least one therapeutic transducer element being configured so as to be utilizable for only therapy, wherein said casing has an outer or exterior surface, said two imaging transducer elements being located inwardly from said outer or exterior surface and disposed at inclined angles relative to said outer or exterior surface of said casing.

9. The probe defined in claim 8 wherein said holder is provided with a plurality of faces, said holder being rotatably mounted in said casing so that different ones of said faces may be alternately positioned adjacent to and facing said window, said at least one therapeutic transducer element being provided on a first one of said faces.

10. The probe defined in claim 9 wherein said first one of said faces is oriented at a non-zero angle relative to said second one of said faces.

11. The probe defined in claim 8 wherein said casing has a first longitudinal axis and said holder has a second longitudinal axis extending parallel to said first longitudinal axis, said at least one therapeutic transducer element being disposed along a side of said holder, said holder being longitudinally reciprocatable relative to said casing so that said at least one therapeutic transducer element is alternatively disposable adjacent said window.

12. The probe defined in claim 8, further comprising an acoustic focusing lens mounted at least indirectly to said casing adjacent to said window.

13. The probe defined in claim 8 wherein said two imaging transducer elements are fixed to said casing adjacent said window.

* * * * *

UNITED STATES PATENT AND TRADEMARK OFFICE
CERTIFICATE OF CORRECTION

PATENT NO. : 10,039,566 B2
APPLICATION NO. : 14/192297
DATED : August 7, 2018
INVENTOR(S) : Yegor Sinelnikov It is certified that error appears in the above-identified patent and that said Letters Patent is hereby corrected as shown below:

In the Claims

Column 20; Claim 7; Lines 54-58 currently read:
wherein said casing has an outer or exterior surface, said two imaging transducer elements being located inwardly from said outer or exterior surface and disposed at inclined angles relative to said outer or exterior surface of said casing.

Should read:
wherein said casing has an outer or exterior surface, said imaging transducer element being located inwardly from said outer or exterior surface and disposed at an inclined angle relative to said outer or exterior surface of said casing.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*